US009651534B1

(12) United States Patent
Ehlert et al.

(10) Patent No.: US 9,651,534 B1
(45) Date of Patent: May 16, 2017

(54) OPTICAL CHEMICAL TEST SYSTEMS AND METHODS

(71) Applicant: Sani-Hawk Optical Solutions LLC, Lake Geneva, WI (US)

(72) Inventors: Brian Ehlert, Lake Geneva, WI (US); David A. Uhen, Burlington, WI (US)

(73) Assignee: Sani-Hawk Optical Solutions LLC, Lake Geneva, WI (US)

( * ) Notice: Subject to any disclaimer, the term of this patent is extended or adjusted under 35 U.S.C. 154(b) by 0 days.

(21) Appl. No.: 14/956,610

(22) Filed: Dec. 2, 2015

(51) Int. Cl.
*G06K 9/36* (2006.01)
*G01N 33/18* (2006.01)
(Continued)

(52) U.S. Cl.
CPC ........... *G01N 33/182* (2013.01); *G01N 21/78* (2013.01); *G01N 21/80* (2013.01); *G01N 33/18* (2013.01);
(Continued)

(58) Field of Classification Search
CPC ................... G06T 7/408; G06T 7/0081; G06T 2207/10024; G06T 7/0004; G06K 9/4652; G06F 17/3025; G06F 17/30243
See application file for complete search history.

(56) References Cited

U.S. PATENT DOCUMENTS 4,113,353 A * 9/1978 Matsushita ............ G06F 3/042 250/227.31
4,268,119 A * 5/1981 Hartmann .......... G02B 27/1013 348/338
(Continued)

FOREIGN PATENT DOCUMENTS

CA 2 253 941 6/1998
DE 44 15 823 9/1995
(Continued)

OTHER PUBLICATIONS

KHT-14B Commercial Dishmachine, High Temp Dishmachine, Knight Index Fluid & Metering, webpage printout Sep. 2014.
(Continued)

*Primary Examiner* — Amir Alavi
(74) *Attorney, Agent, or Firm* — Cook Alex Ltd.

(57) ABSTRACT

An optical chemical test system and method detects information from areas of a chemical test component in the field of view of a color camera. The chemical test component can be a card or a strip and has a color change test area that changes in appearance when subjected to a target chemical in solution, which changes are detected by the color camera and used by an electronic control device to calculate a concentration value for the target chemical. Other areas of the chemical test component, when provided, calibrate the concentration value by providing further data that is recognized by the color camera and used by the electronic control device for calibration. The chemical test component can include features such as one or more indicia or locations for optical coding, card or strip identifiers and authenticators, one or more reference color areas and one or more reference white areas. Also, a color changing indicator can be provided for liquid temperature monitoring and determining whether or not a sample falls within an acceptable temperature range and/or for adjusting the displayed concentration to compensate for color shifts caused by variation in the fluid temperature. A housing system, when provided, facilitates use of controlled illumination in place of ambient illumination. The system and method are suitable for incorporation into a dishwashing machine for sanitation monitoring.

24 Claims, 5 Drawing Sheets

(51) Int. Cl.
*G06T 7/00* (2017.01)
*H04N 7/18* (2006.01)
*G06K 7/10* (2006.01)
*G06K 7/14* (2006.01)
*G01N 21/78* (2006.01)
*G01N 21/80* (2006.01)
*G01N 21/77* (2006.01)

(52) U.S. Cl.
CPC ....... *G06K 7/10722* (2013.01); *G06K 7/1417* (2013.01); *G06T 7/0004* (2013.01); *H04N 7/183* (2013.01); *G01N 2021/7759* (2013.01); *G06T 2207/10024* (2013.01); *G06T 2207/30124* (2013.01)

(56) References Cited

U.S. PATENT DOCUMENTS

| | | | | |
|---|---|---|---|---|
| 4,626,898 | A * | 12/1986 | Baba | H04N 5/202 348/279 |
| 5,390,385 | A | 2/1995 | Beldham | |
| 5,518,927 | A | 5/1996 | Malchesky et al. | |
| 5,906,802 | A | 5/1999 | Langford | |
| 6,551,555 | B2 | 4/2003 | Antonoplos et al. | |
| 7,150,284 | B2 | 12/2006 | Aulbers et al. | |
| 7,233,359 | B2 * | 6/2007 | Suda | H04N 5/23212 348/335 |
| 7,773,143 | B2 * | 8/2010 | Feldman | H04N 3/1587 348/272 |
| 7,860,339 | B2 * | 12/2010 | Yamashita | G06T 5/004 345/600 |
| 8,169,622 | B1 | 5/2012 | Reith et al. | |
| 8,269,845 | B2 * | 9/2012 | Fruehwirth | B07C 5/126 348/210.99 |
| 8,401,229 | B2 * | 3/2013 | Hassan-Shafique | G06K 9/00771 348/50 |
| 8,509,473 | B2 | 8/2013 | Wagner | |
| 8,563,320 | B2 | 10/2013 | Tokhtuev et al. | |
| 8,721,801 | B2 | 5/2014 | Smith | |
| 8,748,191 | B2 | 6/2014 | Kraus et al. | |
| 2003/0142316 | A1 | 7/2003 | Schenkl et al. | |
| 2006/0162746 | A1 | 7/2006 | Kuran et al. | |
| 2010/0202920 | A1 | 8/2010 | Otte et al. | |

FOREIGN PATENT DOCUMENTS

| | | |
|---|---|---|
| DE | 10204002 | 8/2003 |
| DE | 20 2004 012 877 U1 | 8/2004 |
| DE | 10 2006 019 422 | 4/2006 |
| DE | 102009032964 | 7/2009 |
| DE | 102010026068 | 5/2010 |
| DE | 10 2010 031 621 | 1/2012 |
| DE | 102011102627 | 5/2012 |
| DE | 102010054447 | 6/2012 |
| DE | 102012209751 | 12/2013 |
| WO | WO97/24147 | 7/1997 |
| WO | WO 01/26697 | 6/2000 |
| WO | WO 02/47530 | 6/2002 |
| WO | WO2004058038 | 7/2004 |

OTHER PUBLICATIONS

Micro Essential Laboratory—Shop Hydrion Products, webpage printout Sep. 2014.
LaMotte.com, webpage printout, Sep. 2014.

* cited by examiner

OPTICAL CHEMICAL TEST SYSTEMS AND METHODS

BACKGROUND

Field of the Disclosure

The present subject matter relates generally to chemical testing of liquid samples and more specifically to optical test systems and methods for general purpose determination of chemical concentration in a liquid solution.

Description of Related Art

Chemical test paper strips are known for use in measuring chemical concentrations, such as pH, water hardness, and concentration of chlorine, ammonia, and many other chemical concentration levels in water and other liquids. Test strips are used in many industrial, medical and environmental applications. Typically, each test strip is delivered with a small color chart for the user to compare and estimate the resulting concentration of chemical in solution. For example, chlorine test strips use potassium iodide as an active ingredient. In the presence of an oxidant such as chlorine, iodide is converted to iodine which then binds to starch molecules in the strip and forms a blue colored complex. In a specific example, test strips of this type are used to verify the correct concentration of chlorine in the rinse water of commercial dish machines used in restaurants.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

The present disclosure includes an appreciation that such prior test strip systems can compromise overall accuracy inasmuch as measurement is dependent on the ability, experience and skill of the user to compare the color of the exposed strip with the color spectrum of the color chart associated with the strip. Accuracy also is affected by exposure to humidity. Also, test strip life can be limited by exposure to light. Further, the degree of color change can be affected by the temperature of the liquid being tested. The degree of color change can be affected by the amount of time between exposure to the liquid and the reading of the resulting color change. Typical color chart systems rely on colors of a printed chart, which printed colors can vary between production runs or fade over time, negatively impacting accuracy in a non-liner and unpredictable manner.

An embodiment or aspect of the present disclosure provides an optical chemical test system that includes a chemical test card or strip, a color camera, and an electronic control device having an input port for the color camera and being associated with a data output component such as a printer, display, memory device or digital data connection. Suitable electronic control devices include a microprocessor-based board but other suitable devices may be used. The electronic control device can be associated with or include a color detection software program for processing color input data to concentration values of a target chemical or multiple target chemicals.

Another embodiment or aspect of the present disclosure provides an optical chemical test system that includes a chemical test card or strip that contains a reactive test area that changes color when in contact with the target chemical in the solution being monitored. When desired, the reactive test area or areas function as multiple indicators for different target chemicals. Also provided are a color camera and an electronic control device having an input port for the color camera and being associated with a data output component such as a printer, display, memory device or digital data connection. Suitable electronic control devices include a microprocessor-based board but other suitable devices may be used. The electronic control device can be associated with or include a color detection software program.

A further embodiment or aspect of the present disclosure provides an optical chemical test system that includes a chemical test card or strip, a color camera and an electronic control device having an input port for the color camera and being associated with a data output component such as a printer, display, memory device or digital data connection. Suitable electronic control devices include a microprocessor-based board but other suitable devices may be used. The electronic control device can be associated with or include a color detection software program. The test card or strip contains a reactive test area that changes color when in contact with the target chemical in the solution being monitored. The chemical test card or strip of this embodiment also contains an optical code that can be automatically read by the camera and electronic control device.

Yet another embodiment or aspect of the present disclosure provides an optical chemical test system that includes a chemical test card or strip, a color camera and an electronic control device having an input port for the color camera and being associated with a data output component such as a printer, display, memory device or digital data connection. The test card or strip contains a reactive test area that changes color when in contact with the target chemical in the solution being monitored. The chemical test card or strip of this embodiment also contains an optical code that can be automatically read by the camera and electronic control device, which optical code contains information including the type of chemical test being performed such as chemical component concentration. Upon exposure to the solution containing the target component, the color camera then captures the color of the reactive test area, and a color detection software program associated with the electronic control device converts the color of the test area into a chemical concentration, such as parts per million of the target chemical.

An additional embodiment or aspect of the present disclosure provides an optical chemical test system that includes a chemical test card or strip, a color camera and an electronic control device having an input port for the color camera and being associated with a data output component such as a printer, display, memory device or digital data connection. The electronic control device can be associated with or include a color detection software program. The test card or strip contains a reactive test area that changes color when in contact with the target chemical in the solution being monitored. The chemical test card or strip of this embodiment also contains an optical code that can be automatically read by the camera and electronic control device, which optical code contains information according to one or more specific categories, including the type of chemical test being performed such as chemical component concentration, an expiration date for the card, a unique serial number for the card for preventing its reuse, an optically recognized indicia for supplying confirmation of authentic test strip or card, and any combinations of these categories.

A further embodiment or aspect of the present disclosure provides an optical chemical test system that includes a chemical test card or strip, a color camera and an electronic control device having an input port for the color camera and being associated with a data output component such as a printer, display, memory device or digital data connection. The test card or strip contains a reactive test area that changes color when in contact with the target chemical in the solution being monitored. A plurality of the test cards or strips are delivered in a stack with an adhesive layer on the card or strip in a pattern to surround the reactive area thereby forming a sealed environment for the reactive portion, with the adhesive layer being between each card or strip in the stack. In this embodiment, at least some of the test cards or strips have an impermeable membrane coating on the back to enhance isolation of the reactive test area from the surrounding environment until put into use by the operator.

Yet another embodiment or aspect of the present disclosure provides an optical chemical test system that includes a chemical test card or strip, a color camera and an electronic control device having an input port for the color camera and being associated with a data output component such as a printer, display, memory device or digital data connection. The electronic control device can be associated with or include a color detection software program. The test card or strip contains a reactive test area that changes color when in contact with the target chemical in the solution being monitored. In this embodiment a plurality of the test cards or strips are delivered in a stack with an adhesive layer on the card or strip in a pattern to surround the reactive area thereby forming a sealed environment for the reactive portion, with the adhesive layer being between each card or strip in the stack.

A further embodiment or aspect of the present disclosure provides an optical chemical test system that includes a chemical test card or strip, a color camera and an electronic control device having an input port for the color camera and being associated with a data output component such as a printer, display, memory device or digital data connection. The test card or strip contains a reactive test area that changes color when in contact with the target chemical in the solution being monitored. A plurality of the test cards or strips are delivered in a stack with an adhesive layer on the card or strip in a pattern to surround the reactive area thereby forming a sealed environment for the reactive portion, with the adhesive layer being between each card or strip in the stack. In this embodiment, at least some of the test cards or strips have an impermeable membrane coating on the back to enhance isolation of the reactive test area from the surrounding environment until put into use by the operator.

An additional embodiment or aspect of the present disclosure provides an optical chemical test system that includes a chemical test card or strip, a color camera and an electronic control device having an input port for the color camera and being associated with a data output component such as a printer, display, memory device or digital data connection. The test card or strip contains a reactive test area that changes color when in contact with the target chemical in the solution being monitored. In this embodiment, the test card or strip has an impermeable membrane coating on the back to enhance isolation of the reactive test area from the surrounding environment until put into use by the operator. This membrane may be of an opaque material that limits light exposure of the reactive area until use is initiated.

Another embodiment or aspect of the present disclosure provides an optical chemical test system that includes a chemical test card or strip, a color camera and an electronic control device having an input port for the color camera and being associated with a data output component such as a printer, display, memory device or digital data connection. The test card or strip contains a reactive test area that changes color when in contact with the target chemical in the solution being monitored. The electronic control device is associated with or includes a color data processing software program that converts the color of the test area as captured by the color camera into a chemical concentration, such as parts per million of the target chemical. The chemical test card or strip of this embodiment also contains one or more reference color areas and/or one or more reference white areas used by the data processing software program to calibrate the calculation of target chemical concentration for the purpose of compensating for ambient light variation that could affect the color of the reactive test area on the card or strip.

A further embodiment or aspect of the present disclosure provides an optical chemical test system that includes a chemical test card or strip, a color camera and an electronic control device having an input port for the color camera and being associated with a data output component such as a printer, display, memory device or digital data connection. The test card or strip contains a reactive test area that changes color when in contact with the target chemical in the solution being monitored. The electronic control device is associated with or includes a color data processing software program that converts the color data of the test area into a chemical concentration, such as parts per million of the target chemical. The chemical test card or strip of this embodiment also contains a color changing indicator for liquid temperature monitoring and determining whether or not a sample falls within an acceptable temperature range and/or for adjusting the displayed concentration to compensate for color shifts caused by variation in the fluid temperature.

Yet a further embodiment or aspect of the present disclosure provides a substantially closed housing containing a color camera and an illumination source, the housing having an opening through which a chemical test card or strip can be inserted by the user. The chemical test card or strip contains a reactive test area or areas provided for changing in color when in contact with a target chemical or chemicals in a solution being monitored, and the user inserts the exposed test card or strip through the opening, and the illumination source and color camera cooperate to capture data associated with the color of the exposed reactive test area or areas. Software converts the collected color data to concentration of each of the target chemicals. When desired, the chemical test card or strip can include one or more indicia or locations for optical coding, card or strip identifiers and authenticators, one or more reference color areas and/or one or more reference white areas, and a color changing indicator for liquid temperature monitoring and determining whether or not a sample falls within an acceptable temperature range and/or for adjusting the displayed concentration to compensate for color shifts caused by variation in the fluid temperature.

Another embodiment or aspect of the present disclosure is a method for optical chemical testing that provides a chemical test card or strip that contains a reactive test area that changes color when in contact with the target chemical in the solution being monitored. When desired, the reactive test area or areas function as multiple indicators for different target chemicals. The chemical test card or strip is exposed to the solution containing one or more target chemicals and then the reactive test area or areas is/are presented to a color camera, data from the color camera are collected and run through color detection software that converts the data reflecting the color of the reactive test area or areas into concentration value or values of the target chemical or chemicals. The method can include associating the software with an electronic control device having an input port for the color camera, and which can include associating a data output component such as a printer, display, memory device or digital data connection.

An additional embodiment or aspect of the present disclosure is a method for optical chemical testing that provides a chemical test card or strip that contains a reactive test area that changes color when in contact with the target chemical in the solution being monitored, as well as one or more colored/white reference areas. When desired, the reactive test area or areas function as multiple indicators for different target chemicals. The chemical test card or strip is exposed to the solution containing one or more target chemicals and then the reactive test area or areas is/are presented to a color camera, data from the color camera are collected and run through color detection software that converts the data reflecting the color of the reactive test area or areas into concentration value or values of the target chemical or chemicals. The software of this embodiment processes predominant color and/or white levels data of each target area, typically in association with use of a median filter, and these color/white level data are used by the software in determining target chemical concentration value or values. The method can include associating the software with an electronic control device having an input port for the color camera, and which can include associating a data output component such as a printer, display, memory device or digital data connection.

An embodiment or aspect of the present disclosure provides a dishwashing machine having an optical chemical test system that includes a chemical test component such as a card or strip, a color camera, and an electronic control device in electronic communication with the color camera and being associated with a data output component such as a printer, display, memory device or digital data connection. Suitable electronic control devices include a microprocessor-based board but other suitable devices may be used. The electronic control device can be associated with or include a color detection software program for processing color input data to concentration values of a target chemical or multiple target chemicals.

A further embodiment or aspect of the present disclosure provides a dishwashing machine having an optical chemical test system that includes a chemical test component such as a card or strip having one or more reactive areas, authentication areas or calibration information areas, along with a color camera and an electronic control device in electronic communication with the color camera and being associated with a data output component such as a printer, display, memory device or digital data connection. Suitable electronic control devices include a microprocessor-based board but other suitable devices may be used. The electronic control device can be associated with or include a color detection software program for processing color input data to concentration values of a target chemical or multiple target chemicals. In this embodiment, the color camera and an illumination source are within a housing with a slot through which the card or strip slides such that the reactive, authentication and/or calibration information area or areas are in the line of sight of the color camera, thereby significantly reducing the risk of ambient illumination inconsistency.

An embodiment or aspect of the present disclosure provides a method and device for checking chlorine levels in swimming pools. Such include an optical chemical test system that features a chemical test component such as a card or strip, a color camera, and an electronic control device in electronic communication with the color camera and being associated with a data output component such as a printer, display, memory device or digital data connection. Suitable electronic control devices include a microprocessor-based board but other suitable devices may be used. The electronic control device can be associated with or include a color detection software program for processing color input data to concentration values of a target chemical or multiple target chemicals.

An embodiment or aspect of the present disclosure provides a method and device for checking chlorine levels in swimming pools. Such include an optical chemical test system that features a chemical test component such as a card or strip, a color camera, and an electronic control device in electronic communication with the color camera and being associated with a data output component such as a printer, display, memory device or digital data connection. Suitable electronic control devices include a microprocessor-based board but other suitable devices may be used. The electronic control device can be associated with or include a color detection software program for processing color input data to concentration values of a target chemical or multiple target chemicals. In this embodiment, the color camera and an illumination source are within a housing with a slot through which the card or strip slides such that the reactive, authentication and/or calibration information area or areas are in the line of sight of the color camera, thereby significantly reducing the risk of ambient illumination inconsistency.

DESCRIPTION OF THE ILLUSTRATED EMBODIMENTS

As required, detailed embodiments of the present disclosure are disclosed herein; however, it is to be understood that the disclosed embodiments are merely exemplary of the disclosure, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
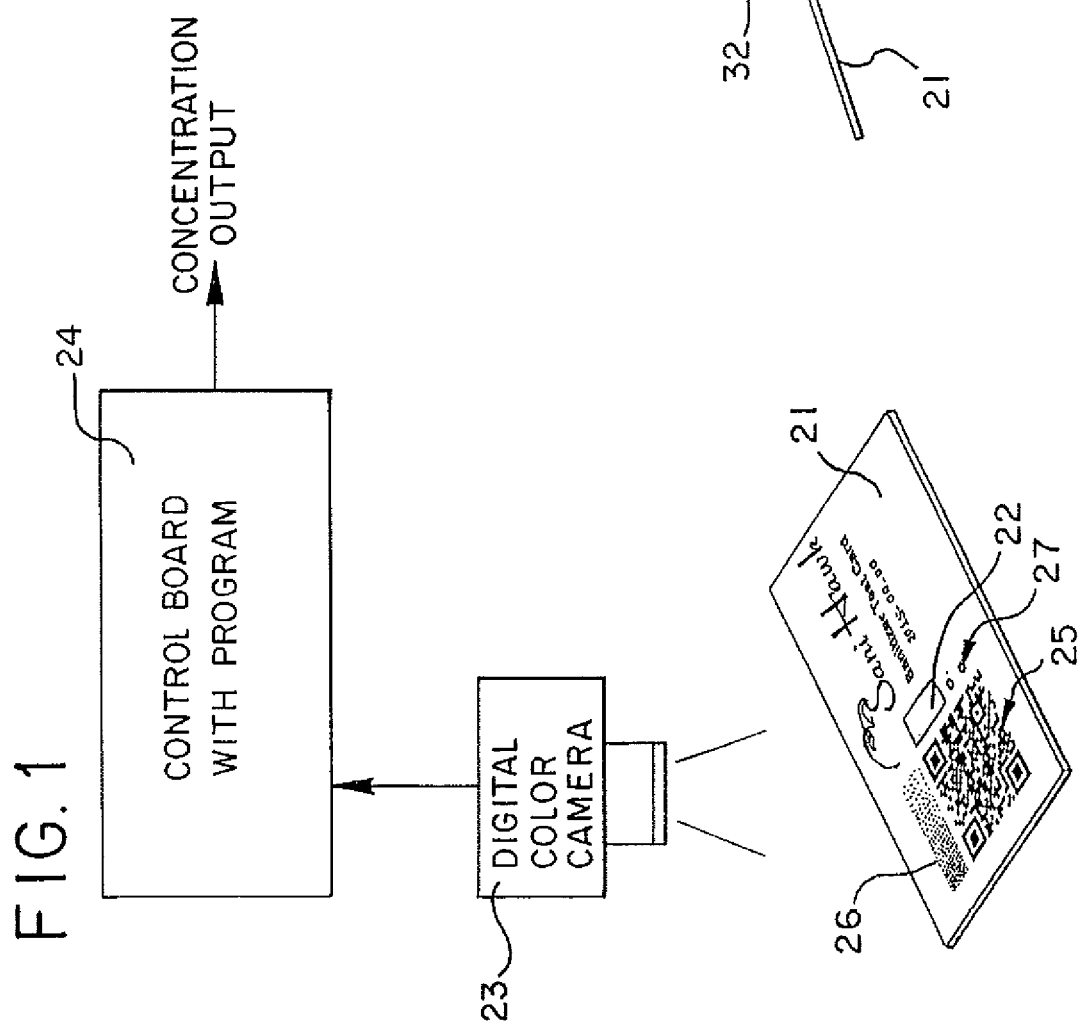
FIG. 1 is a generally schematic illustration of an embodiment of a system of this disclosure.

FIG. 1 illustrates components of embodiments of the optical chemical test system. Included is a chemical test component 21 that can be a card or strip 21 having one or more reactive areas 22, as well as a digital color camera 23 that captures color by encoding each pixel as a combination of colors, and the spectral content of the illumination determines the apparent color of a target area. Also illustrated is a processor 24 that receives and processes data from the color camera into concentration output for one or more target chemicals to which the reactive area or areas 22 of the chemical test component, card or strip is/are exposed. When desired, the chemical test component, card or strip can also include one or more of optical coding indicia 25, reference color areas 26, dots 27 of any shape that are of a material that changes color in response to temperature variation, and combinations thereof.

The color detection software program uses the image captured by the color camera, converting the color of the test area or areas into a chemical concentration, which is in parts per million (ppm) or other suitable concentration units. Test areas of the test components, cards or strips may also contain one or more reference colors and/or white areas that can be used by the color detection software program to calibrate the calculation of chemical concentration. For example, these reference color and reference white areas can generate data detected by the color camera that are used by the data processing system to compensate for variations in ambient lighting that may affect the color of the reactive test area of the test component, card or strip. The test components, cards or strips also can contain color changing indictors for a plurality of chemical species or a color changing indicator for liquid temperature. Multiple indicators can eliminate the need for multiple sampling by combining several tests into one card. A color changing temperature indicator can either be used to determine that the sample falls within an acceptable temperature range or be used to modify the displayed concentration result to compensate for color shifts caused by variation in test sample liquid or fluid temperature.

Suitable optical coding indicia 25 include barcodes or QR codes, and the optical coding indicia contains information on the type of chemical test being performed and other information specific to the card or strip, such as its expiration date, a unique serial number, and other pertinent data. Other optical coding indicia can be provided as an optically recognizable watermark, insignia, logo or other recognition identifier that needs to be recognized by the system and method in order to prevent the operator to substitute a non-compliant sheet or device rather than an authentic test card or strip, to thereby side-step the system. The recognition identifier will prevent thwarting the system by using a piece of paper or device thus found to be incompatible.

An example of a suitable digital color camera 23 is the Mini 800TVL CMOS 6 mm MTV Board Lens CCTV Security Home FPV Tiny Box Color Camera. Another is ELP 2.1 mm Wide Angle Mjpeg 5 megapixel Hd Camera USB for Industrial, camera Module Usb Machine Vision.

Examples of the processor 24 include a microprocessor-based board or a micro-controller-based board. Other devices, arrangements or systems also can be suitable. The processor 24 may itself contain software programming as discussed herein, or any other suitable approach can be utilized to carry out the objectives and tasks of the present disclosure.

Figure 2:
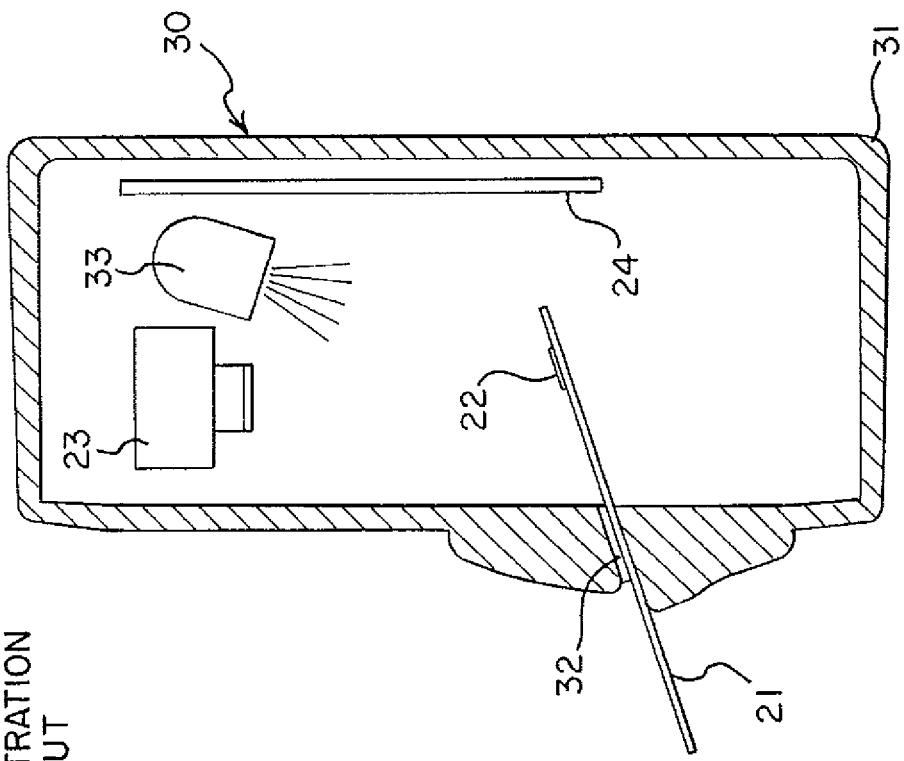
FIG. 2 is a cross-sectional view of an embodiment of the disclosure wherein certain components are shielded from variations in ambient light.

FIG. 2 illustrates embodiments wherein components of an optical tester, generally designated at 30, are arranged within a housing 31 that substantially eliminates variation in illumination conditions under which the color camera 23 collects data from the exposed reactive area or areas 22 by virtue of same being closed to outside light except for a slot 32 in a wall of the housing that provides access for the test card or strip into the inner volume of the otherwise light-impervious housing whereby the reactive area or areas 22 or other area for providing pertinent information as noted herein are in a viewing orientation with respect to the color camera. The processor 24 is shown within the closed volume of the housing, although same can instead be located outside of the housing at a convenient remote area facilitated by suitable communication options such as hard wiring, wireless and other communication approaches. In order to facilitate collection of color data by the color camera, an illumination source 33 can be provided to impart illumination within the housing. Typical illumination sources 33 include LED or other illumination devices or equipment. The approach of a substantially closed housing and an internal illumination source eliminates inaccuracies in reading caused by variations in ambient light.

Figures 3, 4:
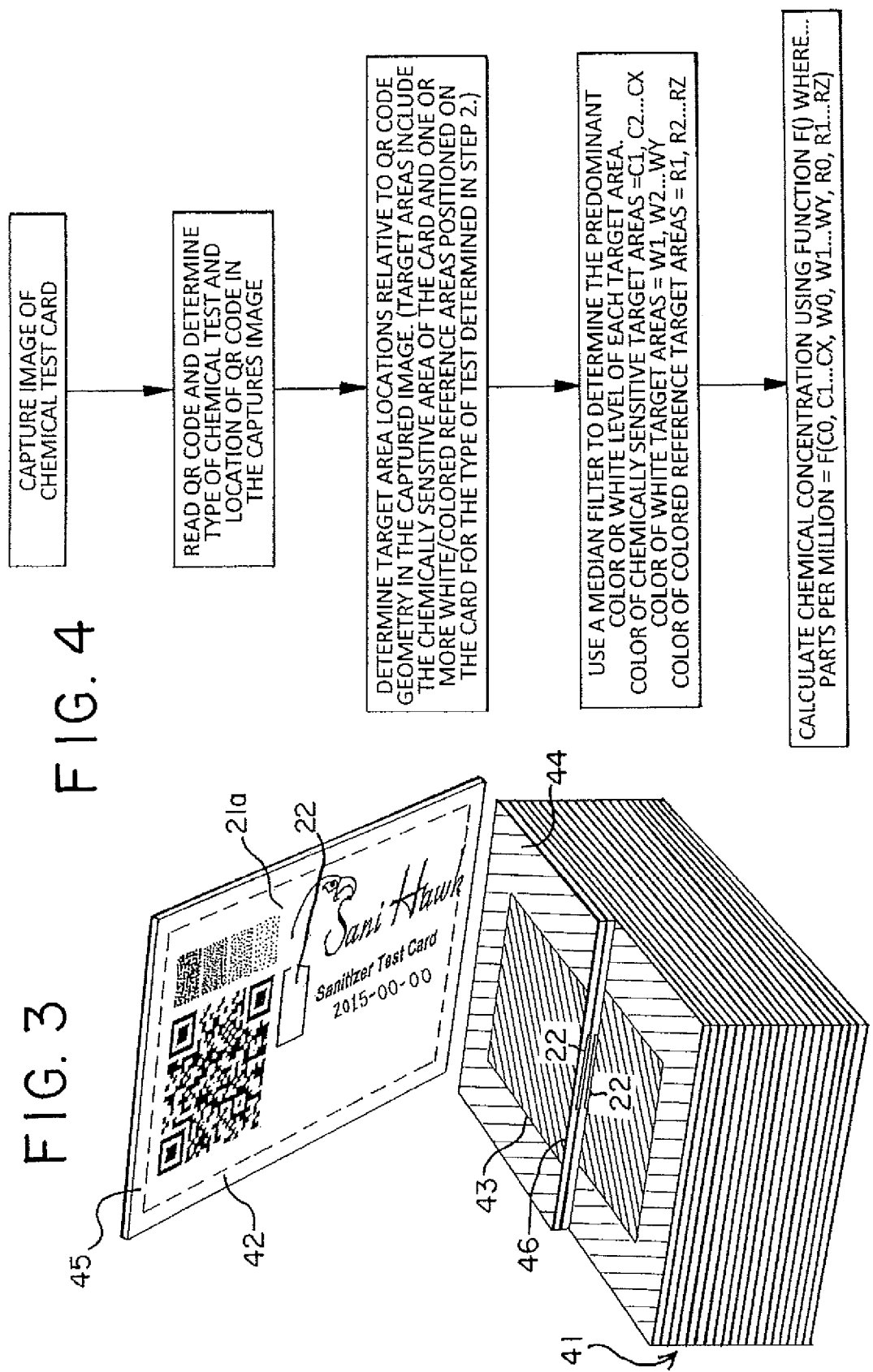
FIG. 3 is a perspective view, partially in cross-section, of an embodiment of the disclosure wherein a plurality of chemical test cards are stacked in booklet form.
FIG. 4 is a flow chart related to an embodiment of the disclosure directed toward chemical concentration calculation.

FIG. 3 illustrates embodiments for color cards or strips that have objectives of protecting and maintaining viability of the color cards or strips for extended periods of time. A plurality of color cards or strips 21a are presented in the form of a booklet, generally designated at 41, such as in the stacked array shown in FIG. 3. The booklet 41 of cards or strips 21a creates a sealed area between individual cards or strips to protect the reactive areas 22 from ambient light and humidity conditions. In the embodiment illustrated in FIG. 3, the card or strip is typically constructed on a substrate 42 of paper, cellulosic, plastic and/or polymeric material, the substrate supporting the reactive area or areas 22 on its front face or surface, while also supporting a raised layer 44 on its back face or surface. A back liner 43 also may be associated with the back face or surface.

The back liner 43, when included, typically is opaque to light and shields the reactive area or areas 22 on each test component, card or strip 21a from ambient light and/or humidity conditions, typically in the environment. Back liner 43 typically is an impermeable membrane, specific examples including Mylar®, polycarbonate and/or polyester. It will be appreciated that the arrangement of the illustrated cards or strips 21a in the booklet 41 is such that the opaque back liner of one card is opposite the reactive area or areas 22 of the adjacent card or strip in the booklet such that the reactive area or areas face an opaque surface. The opaque surface can be provided by dark coloration of the substrate itself, by a layer coated or adhered on the back of the substrate 42. A typical dark color in this regard is black. The liner or membrane 43 can improve the isolation of the reactive test area or areas from surrounding environment until first used by the operator.

When the raised layer 44 is included, same is in a pattern on the card or strip such that it surrounds the reactive area on the card or strip thus forming a sealed environment for the reactive portion. Typically, the raised layer 44 is a peripheral raised layer on one card or strip 21a that engages a front face perimeter 45 of the substrate 42 of another card or strip when in the booklet 41 configuration; in this manner, the raised surface 44 and the perimeter area 45 engage each other, creating a pocket 46 or open space between a front face and a back face adjacent cards or strips 21a. Such a pocket or open space set out in a back surface of one card or strip is opposite the reactive area or areas 22 and other components the opposing or adjacent card or strip that might be present and otherwise be sensitive to light and moisture or humidity of the environment, and/or susceptible to damage due to physical contact with an adjacent card or strip. Raised surface 44 can be provided by any suitable means, such as unitarily with the substrate, by means of a patterned or peripheral polymeric coating that securely adheres to the substrate, or other suitable arrangements. An example of material for the raised area is an adhesive layer coated onto the substrate, examples being a low-tack adhesive, such as PS-0217 available from Polymer Science or 3M 1070 available from 3M Corporation.

Figure 5:
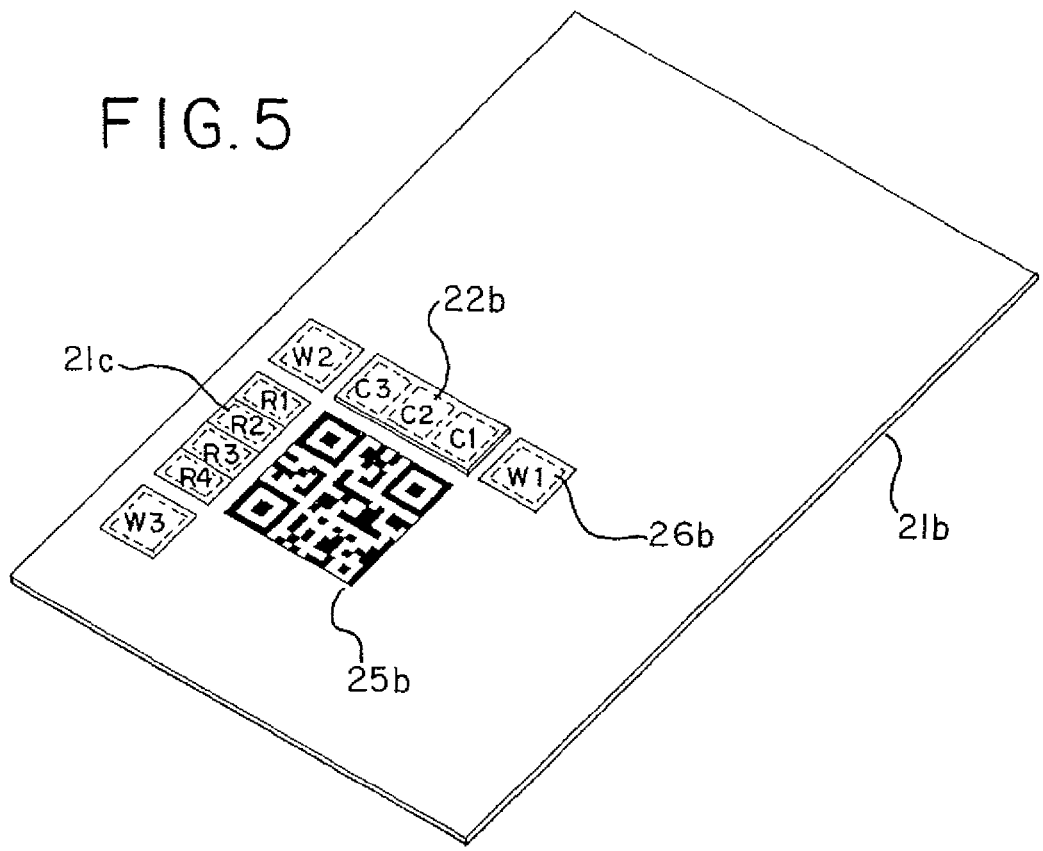
FIG. 5 is a perspective view of a typical chemical test card illustrating coloration factors associated with the flow chart example of FIG. 4.

With further reference to processor 24, same typically includes, provides or is associated with software programming for transforming the data received from the color camera 23 and/or other data sources into concentration information attendant to the target chemical or chemicals to which the test card or strip is exposed during operation of the system of this disclosure. FIG. 4 is an algorithm flow chart for a particular embodiment. In this instance, the data reflect the state of areas of the test card or strip 21b that is illustrated in FIG. 5. FIG. 5 illustrates card or strip 21b having chemically sensitive target areas such as reactive areas 22b (for example C1, C2 and C3) along with reference color areas, for example so-called white reference target areas 26b (for example, W1, W2 and W3) and so-called colored reference target areas 26c (for example, R1, R2, R3 and R4). An optical coding indicia 25b is shown, and color change dots, for example designated 27 in FIG. 1, could also be included but are not illustrated in FIG. 5.

Once the color camera 23 captures the image of the exposed test card or strip 21b, the optical coding indicia 25, such as a QR code, is read in order to determine the type of chemical test and location of the QR code in the captured image. The locations of the target areas such as 22b, 26b and 27b are determined relative to the QR code geometry in the captured image. The coding indicia embeds a code for the type of chemical being monitored and can also embed a unique sequential number for each test component, card or strip. Thus, the system can be used for reading chemical test cards and strips for concentrations including pH, chlorine, sodium hypochlorite, iodine, iodide, quaternary ammonium or other chemicals or compounds in the liquid, typically water.

A median filter is used to determine the predominant color or white level of each target area, such as 22b, 26b and 27b. A median filter is a software component that sorts all of the data from highest to lowest and takes the median value or a group of median values. For the present disclosure, the median third of the data set are taken and then averaged to determine the predominant color of each target area. These data values are inputted to a mathematical function "F" by the software where target chemical concentration level, such as in parts per million, is determined, processed or calculated according to ppm=F(C0 . . . Cx, W0 . . . Wy, R0 . . . Rz). It will be appreciated that the response of the camera, lighting and color change are too non-linear to rely on a full equation; therefore, the present disclosure uses lookup tables for the software. This approach is especially computationally efficient.

An example of the function to calculate concentration of the target chemical(s), such as in parts per million, is based on a determination there is a definable non-linear relationship between chemical concentration and the color of the test areas of the test component, card or strip. The above-noted function F( ) is designed to mathematically model this relationship, even in the presence of non-uniform lighting and/or variations in color camera performance. Color is captured in the digital color camera 23 by encoding each pixel as a combination of red, green and blue. The apparent color of each target area is determined by the spectral content of the illumination, the color filters embedded in the digital color camera sensor, and the white balance setting of the camera's internal software. The white target area or areas 26b (W1, W2, W3 in this example) of the test card or strip are used for the first order of compensation for these variations. In an example, the simplest case uses a single white target area and a single target are of the color changing portion of the card or strip to measure the values Rw, Gw and Bw (white level Red, Greeen, Blue) and Rc, Gc and Bc (color level Red, Green, Blue). From these values so-called "normalized" ratios are calculated as follows: $Rr=Rc/Rw$; $Gr=Gc/Gw$; and $Br=Bc/Bw$.

Figure 6:
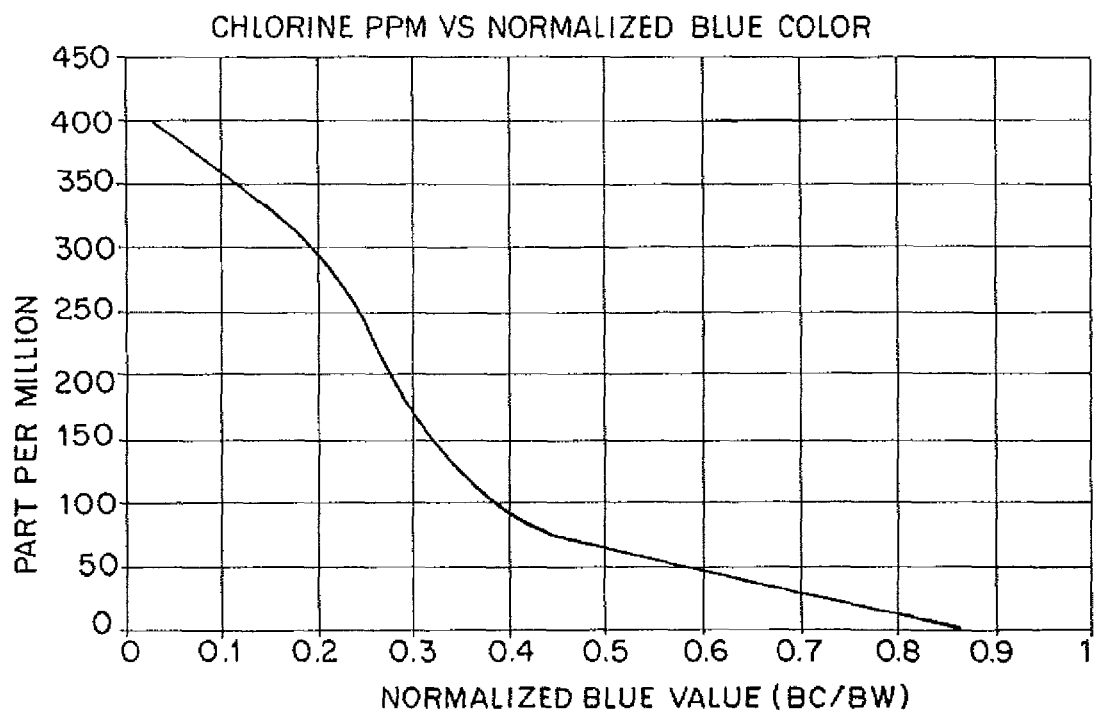
FIG. 6 is a plot of data comprising a lookup table for a particular test chemical and color value.

A minimal system for detecting chlorine concentration, for example, in water can use only the blue value Br. This minimal system is simplified to deal with a single color, and a feature of the disclosure is the disclosure's determination that blue color has the largest amount of sensitivity to chlorine and displays the greatest change attendant to chlorine concentration or content. This approach is followed in order to determine ppm. For this simplest of systems, the function F( ) calculates Br and then uses a lookup table to convert the normalized blue value (or Bc/Bw) to parts per million. The contents of the lookup table for this example are plotted in the table of FIG. 6 as chlorine ppm versus normalized blue color.

Figure 8:
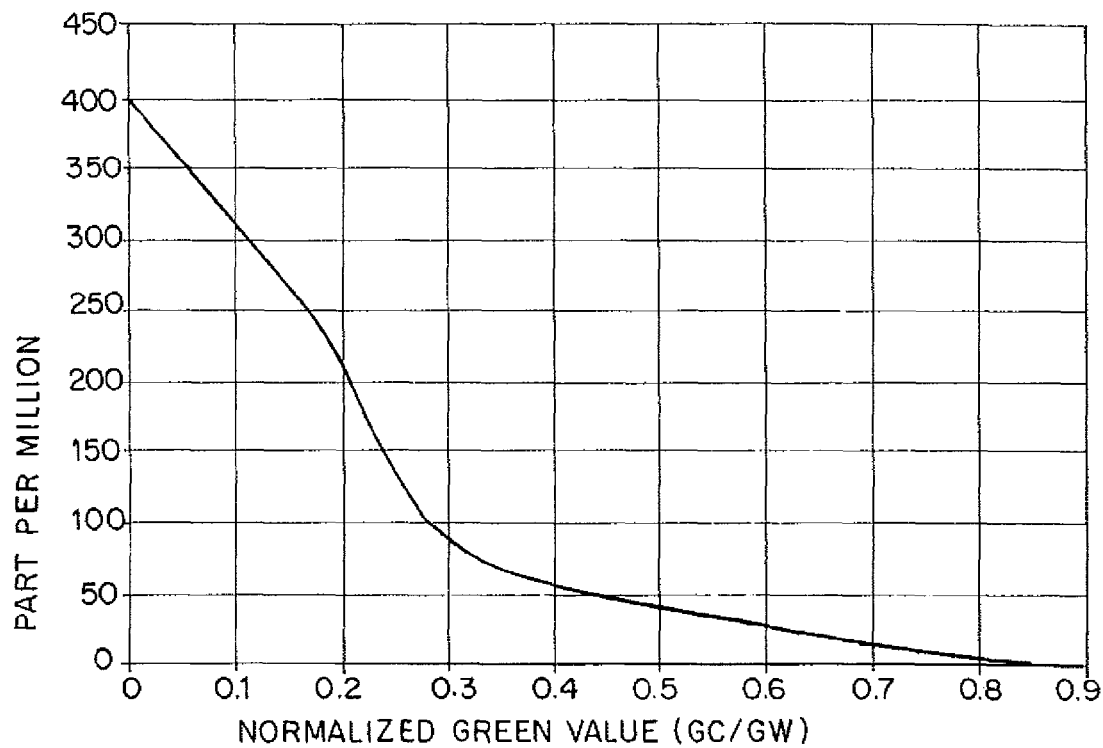
FIG. 8 is a plot of data comprising color density versus temperature regarding optical density.

As an illustration of further data that can be used in connection with this feature, FIG. 8 is a plot of the green response in terms of chlorine concentration (ppm) versus normalized green color. Thus, this plot can be considered to be that of a lookup table focused on the color green as it can be detected by the digital color camera 23. This gives a plot showing the relationship between ppm concentration and the green color read when green is implemented according to this feature of the disclosure.

The additional ratios Rr and Gr can be used in combination with Br as a quality check for the reading. For example, large Gr values in the absence of large Br values indicate that the test component, card or strip sampled is defective since the color detected for same is more green than blue. Test cards or strips for other chemicals would use a similar non-linear fit between predominant color change and concentration level for the chemistry of such other chemicals.

Additional white target areas can be used to compensate for non-uniform illumination of the card. In many lighting conditions, the illumination pattern will form a gradient of light across the card or strip, resulting in a "light" and a "dark" end of the test area. For this case, two or more white targets and multiple targets within the test area can be used according to the following arrangement.

$Bw1$=White level of target area W1 (blue channel).
$Bw2$=White level of target area W2.
$Bc1$=Color of area C1.
$Bc2$=Color area of C2.
$Bc3$=Color area of C3.

As an example, by utilizing Bw1 and Bw2 along with the center distances between target areas, it is possible to calculate a "virtual" white level for each target area within the color changing area or areas. Such calculations follow.

$$Bwc1=Bw1+[Bw2-Bw1]\times(\text{Distance from } W1 \text{ to } C1)/(\text{Distance from } W1 \text{ to } W2)].$$

$Bwc2=Bw1+[(Bw2-Bw1)\times(\text{Distance from } W1 \text{ to } C2)/(\text{Distance from } W1 \text{ to } W2)].$ $Bwc3=Bw1+[(Bw2-Bw1)\times(\text{Distance from } W1 \text{ to } C3)/(\text{Distance from } W1 \text{ to } W2)].$ These "virtual" white levels then are used to calculate three color rations according to the following.

Rbc1=Bc1/Bwc1; Rbc2=Bc2/Bwc2; Rbc3=Bwc3. These three ratios then are combined into a single average color ratio that is used for the calculation of concentration level (e.g. ppm) using the lookup table.

Concerning the reference color targets 26, they are useful in enhancing accuracy of the concentration level determination. These are pre-printed on the component, card or strip to provide color areas or patches designed to mimic the color change of the chemical test area for specific concentrations of the target chemical. The data of the relevant lookup table, or their plotted curve, are modified to fit the colors picked up in the associated target areas (for example R1, R2 . . . Rz). Only then would the data or their plot curve be used to look up the concentration using the Br of the color changing test area. This effectively provides a calibration for the color content of the illumination and the color response of the camera.

More particularly, the reference color patches, when used, calculate Br, Gr and Rr for a known concentration value. This can be used as a real-time check on the lookup table of FIG. 6, for example. As an illustration, if a color patch or reference color target 26 is present, same displays the exact color to be expected according to this aspect of the disclosure, such as for a 100 ppm sample, and the colors can be used to determine from this patch to look up its concentration value. If slightly off due to the ambient lighting or a change of camera output or white balance, this difference is available and usable to scale the table for a more accurate result.

Figure 9:
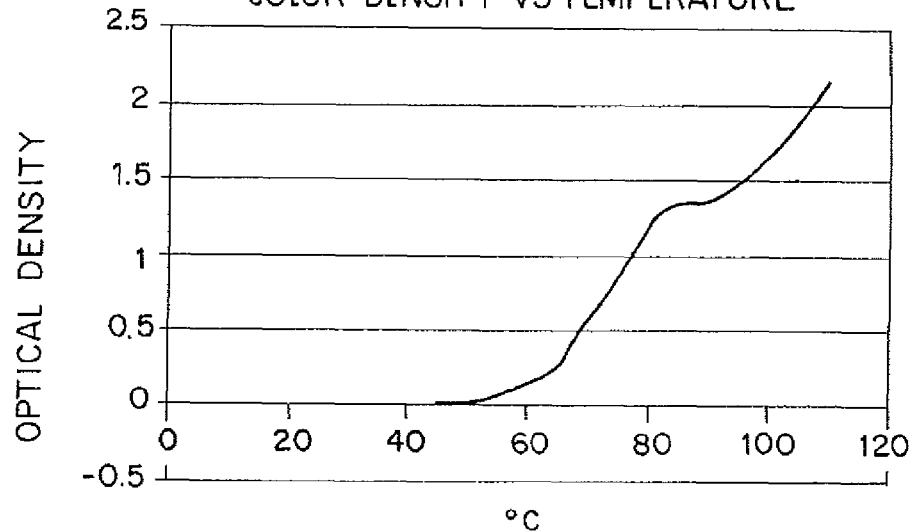
FIG. 9 is a plot of data comprising color density versus temperature regarding optical density from Hallcrest.

With further reference to the areas 27 such as dots that change color in response to temperature to which they are subjected, the disclosure recognizes an identifiable relationship between the intensity of the color change on the test components, cards or strips and the temperature of the liquid or solution containing the target chemical. As an example, chlorine test indicators display darker colors when the liquid of the sample is less than 120° F., while temperatures above 160° F. dramatically reduce the levels of color change. By incorporating the color-changing dots 27, on the test components, cards or strips, the liquid or solution water temperature is determined at the same time as the chlorine concentration (in this example). Armed with this temperature, appropriate adjustments or calibrations can be made to adjust for temperature variations. For example, temperature variation can occur and adjustments will be beneficial in uses where the solution or liquid being monitored is of an elevated temperature that can vary depending on particular environmental or machine conditions. An example is dishwashing equipment Color-changing areas 27 or dots are made from permanent change thermochromatic ink such as that produced by LCR Hallcrest or Smarol Industry. Examples are LCR Hallcrest Thermochromatic ink (http://www.hallcrest.com/our-products/special-effect-ink-coating/thermochromic-permanent-change-ink) and Smarol Industries Irreversible Thermochromic Pigment (http://www.smarol.com/Irreversible-Thermochromic-Pigment.html). Once the color of the dot is determined, a lookup table is used to calculate the water temperature. FIG. 9 is a plot from Hallcrest showing the relationship between temperature and the color changing area or paint or ink. The water temperature then is used to adjust the curve used to relate concentration value to the color of the test area of the card or strip. One simplified yet effective temperature compensation algorithm shifts the curve left or right by the factor: $0.1*(T-130° F.)/10$. This results in higher concentration (e.g. ppm) readings for the same color but higher test liquid temperatures and lower concentration (e.g. ppm) readings for the same color at lower test liquid temperatures.

In a particular embodiment, the optical chemical test system and method are applied to dishwashing machines, finding particular advantage as an optical verification system for dishwashing machines that forces the operator to verify the sanitation of a dishwashing machine after some predetermined time interval of use other time limitation. Generally, good practices and regulations require dishwashing machine operators to verify sanitation usually at the beginning of each shift, after some time interval or number of cycles, or combination of criteria. Usually, sanitation criteria are in terms of ppm, often accomplished by using chlorine test strips that are dipped into the final rinse solution. In the usual approach, the chlorine strip must have a purple color corresponding to a visual color chart. In actual practice, proper sanitation testing and compliance are not always consistently accomplished.

With the dishwashing machine embodiments, the software program of the present disclosure can include paths to keep track of time or cycle count, being connected to the dishwashing machine. When desired, the present system can include electronic control to disable the dishwashing machine when non-compliance is indicated. The reactive area 22 of the cards or strips changes color when contacted with the designated sanitizing chemical in the rinse water, and the present system monitors sanitizing chemical concentration and reports non-compliance and/or removes power to the machine to prevent further use for dishwashing until corrective action is taken.

All of the features discussed herein with respect to the general application of the system and method can be incorporated when the system and method are used in connection with dishwashing machines. These include incorporating an alarm to an output port of the electronic control component. The alarm may be audible, visible, or both, and when activated informs the dishwashing machine operator to insert a chemical test card or strip into the final rinsing solution. The thus exposed test card or strip is presented to the color camera or inserted into the slot or opening if the housing embodiment is practiced. The color camera collects data and the software program determines concentration of the sanitizer or sanitizer component. If the color data comparison and/or calculation indicate adequate concentration, the dishwashing machine will continue operation, but if not the power to the dishwashing machine will be disabled. Sanitizing components that can be monitored for dishwashing machines include pH, sodium hypochlorite, iodine, iodine quaternary ammonium, and other sanitizing compounds, in a water solution.

Figure 7:
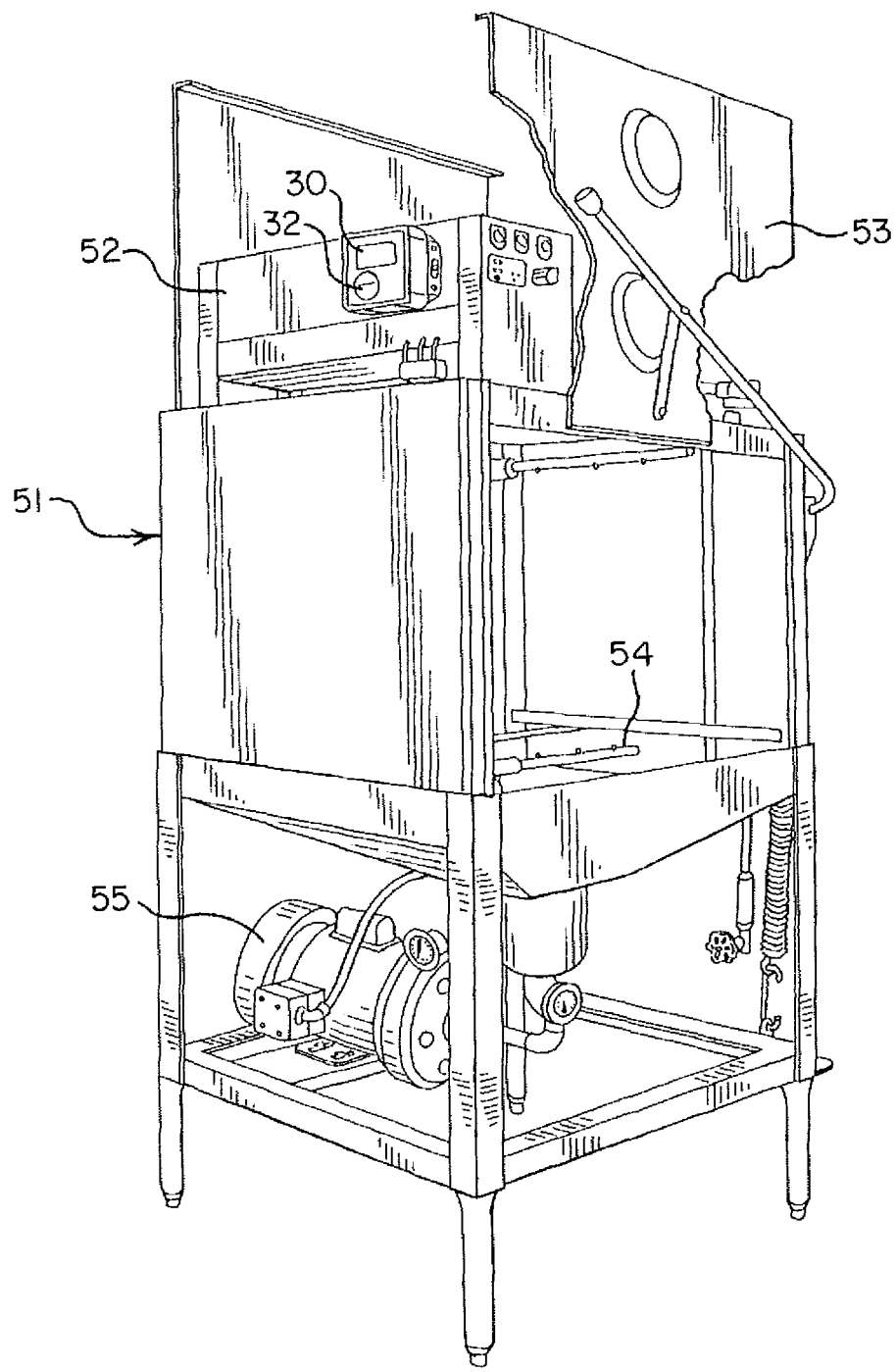
FIG. 7 is a perspective view of a dishwashing machine having an optical chemical test system.

An example of a dishwashing machine, generally designated at 51, according to the present disclosure is illustrated in FIG. 7. Same incorporates an optical tester 30 with slot 32 for receiving the chemical test component 21 (FIG. 2). The optical tester 30 operates as disclosed herein. Also shown are typical dishwasher machine controls 52, a dishwashing machine door 53, a spray bar 54 and a pump 55.

In connection with the device of the disclosure and its optical path features and software and its functions, inputs and outputs, accomplish the advantage of enhanced accuracy over prior systems and at a level that consistently tracks well with control results achieved according to chemical titration of dishwasher water in a unit such as illustrated in FIG. 7.

Features as generally disclosed herein can be suitably used in connection with checking of chlorine levels in swimming pools. For example, the housing of FIG. 2 can be in the vicinity of, or attached to, a swimming pool. The chemical test component 21 is inserted into, or otherwise exposed to, water of a swimming pool and subjected to testing according to the present disclosure. For example, the chemical test component 21 can then be inserted into a housing slot fashioned after the slot 32 in FIG. 2. Then a processor within a housing or otherwise situated in data-passing communication with the optical camera operates on data input to it to determine whether or not the chlorine level is in accordance with an acceptable range for that swimming pool. If outside the range, a signal is given to indicate non-compliance. This can include instructions for rectifying any divergence from such acceptable range or ranges.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An optical chemical test system comprising:
a color camera that detects information in its field of view;
an electronic control device associated with software that processes color detection data;
a chemical test component having a reactive test area that changes in appearance when in contact with a target chemical in a solution;
the color camera detects information from the reactive test area, including after contact with the target chemical, the information from the color camera being received by the electronic control device; and
the software processes the information from the color camera into data providing a concentration value associated with the target chemical.

2. The optical system according to claim 1, wherein the chemical test component further includes, in addition to the reactive test area, a further area readable by the color camera, and the further area is selected from the group consisting of the type of chemical test associated with that chemical test component, an expiration date of the chemical test component, a unique serial number for preventing re-use of the chemical test component, optically recognized authentication indicia, white reference target area, colored reference target area, temperature sensitive dots having coloration dependent on temperature, and combinations thereof.

3. The optical system according to claim 1, wherein the chemical test component is a card or strip, and the reactive test area changes color when in contact with the target chemical of the solution being monitored.

4. The optical system according to claim 3, wherein the software includes color data conversion processing that converts the color of the test area as captured by the color camera into the concentration value of the target chemical.

5. The optical system according to claim 4, wherein the card or strip includes one or more reference areas selected from the group consisting of one or more white reference target areas, one or more colored reference target areas, and combinations thereof, and wherein the color camera recognizes information from the reference areas, and the software color data conversion processing calibrates the concentration of the target chemical from the thus recognized information.

6. The optical system according to claim 5, wherein color camera information from the reference target area and a lookup table combine to correct for accuracy in concentration determination.

7. The optical system according to claim 4, wherein the card or strip includes a color changing indicator that shifts in coloration in response to temperature change, wherein the color camera detects any shift in coloration of this indicator, and wherein the software determines whether or not the solution of the target chemical falls within an acceptable temperature range and adjusts the concentration of the target chemical.

8. The optical system according to claim 4, wherein the card or strip includes optical coding indicia, and the software processes information of the optical coding indicia for authentication of the card or strip.

9. The optical system according to claim 1, further including a substantially enclosed housing having an internal volume, the chemical test component is a card or strip, and a slot of the enclosed housing provides access for the card or strip into the housing such that the reactive test area is within the internal volume of the housing, the color camera being within the internal volume of the housing, and an illumination source providing illumination within the internal volume of the housing.

10. The optical system according to claim 9, wherein the chemical test component further includes, in addition to the reactive test area, a further area readable by the color camera, and the further area is selected from the group consisting of the type of chemical test associated with that chemical test component, an expiration date of the chemical test component, a unique serial number for preventing re-use of the chemical test component, optically recognized authentication indicia, white reference target area, colored reference target area, temperature sensitive dots having coloration dependent on temperature, and combinations thereof.

11. The optical system according to claim 9, wherein the card or strip includes one or more reference areas selected from the group consisting of one or more white reference target areas, one or more colored reference target areas, and combinations thereof, and wherein the color camera recognizes information from the reference areas, and the software color data conversion processing calibrates the concentration of the target chemical from the thus recognized information.

12. The optical system according to claim 9, wherein the card or strip includes a color changing indicator that shifts in coloration in response to temperature change, wherein the color camera detects any shift in coloration of this indicator, and wherein the software determines whether or not the solution of the target chemical falls within an acceptable temperature range and adjusts the concentration of the target chemical.

13. The optical system according to claim 9, wherein the card or strip includes optical coding indicia, and the software processes information of the optical coding indicia for authentication of the card or strip.

14. The optical system according to claim 1, wherein the software includes a median filter component included in determining a predominant color for a target area.

15. The optical system according to claim 1, wherein the system is associated with a swimming pool and wherein the chemical test component is configured and engineered to check on concentration value of a target chemical within water of the swimming pool.

16. A dishwashing machine having an optical chemical test system, comprising:
an enclosure for holding dishes and the like, a source of water into the enclosure, a body of post-washing rinse water, and an optical chemical test system that monitors water of the rinse water, the optical chemical test system comprising:
a color camera that detects information in its field of view;
an electronic control device associated with software that processes color detection data;
a chemical test component having a reactive test area that changes in appearance when in contact with a target chemical in the rinse water;
the color camera detects information from the reactive test area, including after contact with the target chemical of the rinse water, the information from the color camera being received by the electronic control device; and
the software processes the information from the color camera into data providing a concentration value associated with the target chemical.

17. The dishwashing machine according to claim 16, wherein the chemical test component is a card or strip, and the reactive test area changes color when in contact with the target chemical of the solution being monitored, wherein the software includes color data conversion processing that converts the color of the test area as captured by the color camera into the concentration value of the target chemical.

18. The dishwashing machine according to claim 17, wherein the card or strip includes one or more reference areas selected from the group consisting of one or more white reference target areas, one or more colored reference target areas, and combinations thereof, and wherein the color camera recognizes information from the reference areas, and the software color data conversion processing calibrates the concentration of the target chemical from the thus recognized information.

19. The dishwashing machine according to claim 17, wherein the card or strip includes a color changing indicator that shifts in coloration in response to temperature change, wherein the color camera detects any shift in coloration of this indicator, and wherein the software determines whether or not the solution of the target chemical falls within an acceptable temperature range and adjusts the concentration of the target chemical.

20. The dishwashing machine according to claim 17, wherein the card or strip includes optical coding indicia, and the software processes information of the optical coding indicia for authentication of the card or strip.

21. A method for optical chemical testing, comprising:
providing a chemical test component having a reactive test area that changes in color when in contact with a target chemical in solution;
subjecting the reactive test area of the chemical test component to a solution having the target chemical;
positioning a color camera with respect to the reactive test area and optically collecting color-change information from the reactive test area;
providing an electronic control device, and transmitting thereto the color-change information from the reactive test area collected by the color camera; and
converting by operation of the electronic control device the color-change information from the reactive test area to a concentration value associated with the target chemical.

22. The method according to claim 21, wherein the providing of the chemical test component includes providing one or more reference areas selected from the group consisting of one or more white reference target areas, one or more colored reference target areas, and combinations thereof;
recognizing by the color camera information from the reference areas; and
applying the information from the reference areas to the electronic control device color data conversion processing using same for calibrating the concentration value of the target chemical.

23. The method according to claim 21, wherein the providing of the chemical test component includes a color changing indicator that shifts in coloration in response to temperature change;
detecting with the color camera any shift in coloration of this indicator due to temperature;
determining from the shift by operation of the electronic control device whether or not the solution of the target chemical falls within an acceptable temperature range; and
adjusting as necessary the concentration value of the target chemical if the acceptable temperature range is not detected.

24. The method according to claim 21, wherein the providing of the chemical test component includes an optical coding indicia;
detecting the optical code indicia with the color camera;
determining from the optical code indicia whether or not the chemical test component is an authentic chemical test component; and
continuing with the method to determine the target chemical concentration value if the chemical test component is authenticated, or ceasing the method to determine the target chemical concentration value if the chemical test component is not authenticated.

* * * * *